United States Patent [19]

Komatsu et al.

[11] 4,281,179

[45] Jul. 28, 1981

[54] PROCESS FOR PRODUCING TEREPHTHALIC ACID WITH HIGH PURITY

[75] Inventors: Makoto Komatsu; Toru Tanaka, both of Kurashiki, Japan

[73] Assignee: Mitsubishi Gas Chemical Company, Inc., Tokyo, Japan

[21] Appl. No.: 119,969

[22] Filed: Feb. 8, 1980

Related U.S. Application Data

[63] Continuation of Ser. No. 967,091, Dec. 6, 1978, abandoned.

[30] Foreign Application Priority Data

Dec. 7, 1977 [JP] Japan ................................ 52-146935

[51] Int. Cl.$^3$ ............................................. C07C 51/16
[52] U.S. Cl. .................................................... 562/416
[58] Field of Search ................................ 562/421, 416

[56] References Cited

U.S. PATENT DOCUMENTS

| 2,907,792 | 10/1959 | McIntyre | 562/421 |
| 3,012,038 | 12/1961 | O'Neill et al. | 562/421 |
| 3,944,601 | 3/1976 | Kuhlmann | 562/416 |

Primary Examiner—Alan Siegel
Attorney, Agent, or Firm—Armstrong, Nikaido, Marmelstein & Kubovcik

[57] ABSTRACT

Terephthalic acid with a high purity and high whiteness is produced by oxidizing p-tolualdehyde with molecular oxygen such as air in the presence of a heavy metal catalyst of manganese and/or cerium, a bromine compound, and a mineral acid in water as a solvent at a bromine compound concentration of 0.5–12% by weight on the basis of the reaction solution in terms of bromine ions and at a ratio of g-equivalents of hydrogen ions of the mineral acid to sum total of g-equivalents of the hydrogen ions and manganese and/or cerium ions of 1–85% and at a ratio of sum total of g-equivalents of the hydrogen ions and manganese and/or cerium ions to g-equivalents of bromine ions of 0.5–5. Terephthalic acid thus produced is directly polymerizable with glycols without any purification.

15 Claims, No Drawings

PROCESS FOR PRODUCING TEREPHTHALIC ACID WITH HIGH PURITY

This is a continuation, of application Ser. No. 967,091, filed Dec. 6, 1978 now abandoned.

This invention relates to a process for producing terephthalic acid by oxidizing p-tolualdehyde with molecular oxygen in the presence of water as a solvent.

Japanese Patent Publication No. 13921/64 (British Patent Specification No. 833,438) discloses a process comprising oxidizing an aromatic compound containing an alkyl substituent or a partially oxidized alkyl substituent in water as a solvent in the presence of a bromine ion.

Further, Japanese Laid-open Patent Application No. 4019/71 (U.S. Pat. No. 3,678,106) discloses a process for producing terephthalic acid by oxidizing p-toluic acid in water as a solvent, the water containing hydrogen bromide. The processes based on oxidation reaction in water as the solvent are excellent, because there are no such problems as loss of the solvent by combustion during the reaction, etc., but there have been disclosed no specific examples of oxidation of tolualdehyde in water as the solvent, and thus no knowledge has been obtained as to catalysts and reaction condition that can produce terephthalic acid with a high purity when p-tolualdehyde is oxidized in water as the solvent. When p-tolualdehyde was oxidized under the same conditions as in such prior art processes, it was found that the resulting terephthalic acid contained a large amount of 4-carboxybenzaldehyde (4CBA) as a reaction intermediate or impurities such as coloring impurities of unknown structures, bromine-containing compounds, etc., and only terephthalic acid with a very low purity was obtained. That is, it is impossible to react the terephthalic acid obtained in such piror art process directly with glycols to obtain polyester, and a complicated purification step, such as recrystallization, recrystallization together with hydrogenating reaction, etc. is required for obtaining terephthalic acid for direct polymerization, rendering the process industrially disadvantageous. When the reaction temperature is increased to reduce the content of reaction intermediates including 4CBA as a main component in the resulting terephthalic acid, a decomposition-combustion reaction of p-tolualdehyde is considerably increased in the presence of a single catalyst of hydrogen bromide.

An object of the present invention is to overcome said disadvantages and provide a process for producing terephthalic acid with a high purity in a good yield, using water as the solvent on the basis of a new finding that the purity of terephthalic acid formed under specific conditions can be considerably increased when manganese and/or cerium is employed as a catalyst and both a bromine compound and a mineral acid are employed at the same time.

That is, the present invention provides a process for producing terephthalic acid with a high purity, wherein terephthalic acid is produced by oxidizing p-tolualdehyde with molecular oxygen in the presence of a heavy metal catalyst and a bromine compound in water as a solvent, which comprises conducting the oxidation reaction by using manganese and/or cerium as the heavy metal catalyst, maintaining the bromine concentration in the reaction system during the reaction in a range of 0.5-12% by weight on the basis of the reaction solution in terms of bromine ion, and maintaining the amount of mineral acid in the reaction system during the reaction at a ratio of g-equivalents of hydrogen ions of the mineral acid to sum total of g-equivalents of the hydrogen ions and manganese and/or cerium ions ($H^+/H^+ + 2Mn^{++}$ or $H^+/H^+ + 3Ce^{+++}$) of 1-85% and at a ratio of sum total g-equivalents of the hydrogen ions and manganese and/or cerium ions to g-equivalents of bromine ions ($H^+ + 2Mn^{++}/Br^-$ or $H^+ + 3Ce^{+++}/Br^-$) of 0.5-5.

The heavy metal catalyst used in the present invention is manganese and/or cerium, and it has been confirmed that, when vanadium is used as the heavy metal catalyst, only colored terephthalic acid is produced. It is possible to add these heavy metals in a form of water-soluble salts, but it is desirable to add them in a form of bromide. Precaution must be paid to such a fact that, when they are added in a form of readily decomposable acid salt, for example, acetate, the mineral acid added to the reaction system during reaction is converted to a heavy metal salt, consuming the hydrogen ions originating from the mineral acid.

Any of organic or inorganic bromine compounds can be added to the reaction system, so long as it can produce promine ions during the reaction, but in view of counterpart cations, it is desirable to add it to the reaction system in a form of manganese bromide or cerium bromide, or hydrogen bromide. The amount of bromine ions to be added is, on the basis of the reaction solution, 0.5-12% by weight, preferably 0.5-6% by weight, more preferably 1-4% by weight. In the present invention, the reaction solution means the sum of manganese and/or cerium compounds, bromine compound, mineral acid and water. When the amount of the bromine ions is below 0.5% by weight on the basis of the reaction solution, combustion and decomposition of p-tolualdehyde are remarkable, and the content of 4CBA or coloring impurities in the resulting terephthalic acid is much increased. On the other hand, the presence of bromine ions above 12% by weight, on the basis of the reaction solution, in the reaction system suppresses the reaction.

In the present invention, the presence of hydrogen ions in addition of such combination of the heavy metal catalyst and the bromine compound can considerably increase a catalytic activity. In the present invention, thus, a mineral acid is added to the reaction system at a ratio of g-equivalents of hydrogen ions of the mineral acid to sum total of g-equivalents of the hydrogen ions and manganese and/or cerium ions ($H^+/H^+ + 2Mn^{++}$ or $H^+/H^+ + 3Ce^{+++}$) of 1-85%, preferably 5-75% and at a ratio of sum total of g-equivalents of the hydrogen ions and manganese and/or cerium ions to g-equivalents of the bromine ion ($H^+ + 2Mn^{++}/Br^-$ or $H^+ + 3Ce^{+++}/Br^-$) of 0.5-5, preferably 0.75-4. When the ratio of the hydrogen ions to the sum total of hydrogen ions and manganese and/or cerium ions is outside said range, the desired catalytic effect cannot be obtained and directly polymerizable grade terephthalic acid with a high purity cannot be obtained. When the ratio of the sum total of the hydrogen ions and manganese and/or cerium ions to the bromine ions is outside said range, the catalytic activity is also changed, and terephthalic acid with a good whiteness cannot be obtained.

Any mineral acid can be used in the present invention, so long as it is stable during the reaction, but hydrogen bromide or sulfuric acid is desirable.

Reaction temperature is 180°-280° C., preferably 210°-260° C. If the reaction temperature is below 180°

C., the reaction intermediate 4CBA and coloring impurities are formed unpreferably in a large amount.

Reaction pressure is generally automatically determined by a process of keeping the reaction temperature at a certain value by evaporation and condensing and reflux operation of water as the solvent, but it is possible to keep the reaction pressure at a desired certain value by a heat exchange means from the outside. The pressure range is not particularly restricted, so long as it is in such a range as to keep the reactant in a liquid phase, but usually a pressure range of 10–50 kg/cm² gauge is utilized.

Either oxygen or air can be used as an oxidizing agent, but it is economically advantageous to use air as the oxidizing agent.

It is satisfactory that the amount of water to be used as the solvent is at least twice the weight of the raw material p-tolualdehyde, and particularly preferable that it is 3–6 times the weight of p-tolualdehyde.

Reaction can be carried out by any of batchwise, semi-continuous and continuous operations.

Since water is used as the solvent in the present invention, there are no problems such as loss of a solvent by combustion, etc. as in the case of using acetic acid as the solvent, or the impure, colored terephthalic acid as in using hydrogen bromide as a catalyst is no more obtained. In the present invention, terephthalic acid with a considerably high whiteness and a high purity can be obtained in a distinguished yield, particularly with such an excellent effect that, even if the oxidation reaction of p-tolualdehyde is carried out at a temperature above 245° C. permitting a wet combustion to occur, the decomposition and combustion of p-tolualdehyde are negligible. The terephthalic acid obtained according to the present invention can be directly polymerized with glycols without passage through a purification step.

The present invention will be described in detail below, referring to examples.

Polymer color shade used in the following examples is determined by directly polymerizing purified terephthalic acid with ethylene glycol in the well known manner, visually observing a degree of color of the resulting polymer chips, and determining it on the basis of the predetermined color shade of standard product. The color shade is classified into five color groups in the order of increasing coloring degree, i.e. colorless, pale yellow, light yellow, yellow, and brownish yellow. The color shade reflects the presence of a very small amount of coloring materials and color-inducing materials in terephthalic acid, and thus can be used for evaluation of terephthalic acid. It is meant that terephthalic acid whose polymer color shade is indicated as colorless can be directly polymerizable.

EXAMPLE 1

671 g of water, 10.5 g of hydrogen bromide, and 18.8 g of manganese bromide (tetrahydrate) (the amount of the reaction solution was $671+10.5+18.8 \approx 700$ g) were charged into an autoclave having a net capacity of 2 l, provided with a reflux cooler, a stirrer, a heater, a feed inlet, a gas inlet and a product outlet [bromine ion content: 3.0% by weight, ratio of sum total of g-equivalents of hydrogen ions and manganese ions to g-equivalents of bromine ions: $(H^+ + 2Mn^{++}/Br^-)$; 1.0, ratio of g-equivalents of hydrogen ions to sum total of g-equivalents of hydrogen ions and manganese ions $(H^+/H^+ + 2Mn^{++})$: 50%].

Nitrogen gas was introduced under pressure into the autoclave at the gas inlet to increase the pressure of the autoclave to 10 kg/cm² gauge, and then the autoclave was heated to 245° C. by a heater. When the autoclave was heated to 245° C., air was introduced into the autoclave at the gas inlet to replace the nitrogen with the air, and p-tolualdehyde was fed into the autoclave at a rate of 120 g/hr for one hour while blowing the air into the autoclave.

Even after the completion of feeding p-tolualdehyde, the air was continuously blown into the autoclave, and when the oxygen concentration of effluent gas was recovered to 21%, the air blowing was discontinued, and the resulting reaction product was taken out of the autoclave and separated into solid matters and a solution. The solid matters were washed with hot water.

Properties of the resulting terephthalic acid and polymer color shade obtained from the terephthalic acid are givne below:

4CBA—221 ppm
$OD_{340}$—0.076
Polymer color shade—colorless

The term "$OD_{340}$" represents a light absorbancy determined by dissolving 2 g of terephthalic acid in 25 ml of 2 N KOH and measuring a light absorbancy of the resulting solution in a 50 mm cell at 340 mµ, and reflects the content of coloring impurities and coloring-inducing materials in terephthalic acid. The lower value means the presence of less coloring impurities and color-inducing materials.

EXAMPLES 2–5

Oxidation of p-tolualdehyde was conducted under the same reaction conditions as in Example 1, using catalysts whose ratios of counterpart cations, i.e. a ratio of hydrogen ions to sum total of manganese and hydrogen ions were changed while using the same bromine ion content as in Example 1. The results are shown in the following table.

| Example | Hydrogen bromide (g) | Manganese bromide 4H₂O (g) | $H^+/H^+ + 2Mn^{++}$ (%) | Terephthalic acid quality 4CBA (ppm) | $OD_{340}$ | Polymer color shade |
|---|---|---|---|---|---|---|
| 2 | 2.10 | 33.9 | 10 | 340 | 0.150 | colorless |
| 3 | 4.21 | 30.2 | 20 | 256 | 0.107 | colorless |
| 4 | 12.6 | 15.1 | 60 | 216 | 0.083 | colorless |
| 5 | 16.8 | 7.54 | 80 | 224 | 0.148 | colorless |

(700 g of the reaction solution was used throughout all these examples)

COMPARATIVE EXAMPLES 1–4

Tests were carried out under the same conditions with the same bromine ion contents as in Example 1 except those mentioned below. The results are given in the following Table

| Comp. Example | Catalyst (reaction solution: 700 g) | $H^+/H^+ + 2Mn^{++}$ (%) | Terephthalic acid quality 4CBA (ppm) | $CD_{340}$ | Polymer color shade |
|---|---|---|---|---|---|
| 1 | Manganese bromide . 4H₂O 37.7 g High purity terephthalic acid 32 g | 0 | 900 | 1.8 | Brownish yellow |
| 2 | Only hydrogen | 100 | 560 | 0.410 | Yellow |

-continued

| Comp. Example | Catalyst (reaction solution: 700 g) | $H^+/H^+ + 2Mn^{++}$ (%) | Terephthalic acid quality | | Polymer color shade |
|---|---|---|---|---|---|
| | | | 4CBA (ppm) | $CD_{340}$ | |
| | bromide 21.0 g | | | | |
| 3 | Hydrogen bromide 0.42 g Manganese bromide . $4H_2O$ 36.9 g | 2 | 700 | 1.2 | Brownish yellow |
| 4 | Hydrogen bromide 18.9 g Manganese bromide . $4H_2O$ 3.77 g | 90 | 350 | 0.280 | Light yellow |

Comparative Example 1, is an example of oxidation, using only manganese bromide as a catalyst and the bromine ion content in the preferable range of the present invention. Only in Comparative Example 1, high purity terephthalic acid is added to the reaction system from the start of reaction.

Comparative Example 2 is an example of oxidation using only hydrogen bromide as a catalyst and the bromine ion content in the preferable range of the present invention.

Comparative Example 3 is an example of oxidation using a catalyst system of hydrogen bromide and manganese bromide, where the manganese ion content is larger than the preferable range of the present invention.

Comparative Example 4 is an example of oxidation, using a catalyst system of hydrogen bromide and manganese bromide, where the manganese ion content is outside the preferable range of the present invention.

EXAMPLE 6

Oxidation of p-tolualdehyde was carried out under the same conditions as in Example 1, using cerium as the catalyst in place of manganese, and using the same bromine ion content as in Example 1.

A reaction solution prepared by adding 20.6 g of cerium bromide.$5H_2O$ and 10.5 g of hydrogen bromide as the catalyst, and making 700 g with water was used. Properties of the resulting terephthalic acid and polymer color shade resulting from the terephthalic acid are given below:
4CBA—190 ppm
$OD_{340}$—0.070
Polymer color shade—Colorless

COMPARATIVE EXAMPLE 5

Reaction and treatment after the reaction were carried out in the same manner as in Example 1, except that only 41.1 g of cerium bromide.$5H_2O$ was used as the catalyst and 32 g of high purity terephthalic acid was added as the acid component to the reaction system before the start of reaction. The amount of water was 659 g.

Properties of the resulting terephthalic acid and polymer color shade resulting from the terephthalic acid are given below:
4CBA—450 ppm
$OD_{340}$—0.500
Polymer color shade—Yellow

EXAMPLES 7–9

Oxidation was carried out under the same reaction conditions as in Example 1, using a catalyst system of hydrogen bromide and manganese bromide, except that the bromine ion content was changed while keeping the hydrogen ion ratio ($H^+/H^+ + 2Mn^{++}$) at 50%. The results are given in the following Table.

| Example | Water (g) | Hydrogen bromide (g) | Manganese bromine . $4H_2O$ (g) | Bromine ion content (%) | Terephthalic acid quality | | Polymer color shade |
|---|---|---|---|---|---|---|---|
| | | | | | 4CBA (ppm) | $OD_{340}$ | |
| 7 | 681 | 5.25 | 9.40 | 1.5 | 230 | 0.080 | Colorless |
| 8 | 656 | 14.0 | 25.1 | 4.0 | 205 | 0.080 | Colorless |
| 9 | 606 | 31.5 | 56.4 | 9.0 | 285 | 0.078 | Colorless |

COMPARATIVE EXAMPLE 6

As a catalyst system, 2.51 g of manganese bromide.$4H_2O$ and 1.4 g of hydrogen bromide were used (bromine ion content: 0.4% by weight). The amount of reaction solution was made to 700 g by adding water to said catalyst system. The reaction was carried out under the same conditions as in Example 1, except the catalyst amounts.

Properties of the resulting terephthalic acid and polymer color shade are given below.
4CBA—1215 ppm
$OD_{340}$—0.440
Polymer color shade—Yellow This is an example of using hydrogen bromide and manganese bromide as catalysts and keeping the hydrogen ion ratio ($H^+/H^+ + 2Mn^{++}$) at 50%, while the bromine ion content is outside the preferable range of the present invention.

EXAMPLE 10

755 g of water, 7.35 g of sulfuric acid, 21.5 g of manganese bromide.$4H_2O$ and 15.5 g of sodium bromide (the amount of reaction solution was 800 g) were fed into an autoclave having a net capacity of 2 l, provided with a reflux cooler, a stirrer, a heater, a feed inlet, a gas inlet and a product outlet (bromine ion content: 3.0% by weight, ratio of sum total of g-equivalents of manganese ions and hydrogen ions originating from the mineral acid to bromine ions ($H^+ + 2Mn^{++}/Br^-$): 1.0, ratio of g-equivalents of the hydrogen ions to sum total of g-equivalents of the hydrogen ions and manganese ions ($H^+/H^+ + 2Mn^{++}$): 50%.

Nitrogen was introduced under pressure into the autoclave at the gas inlet to increase the pressure of the autoclave to 10 kg/cm$^2$ gauge, and then the autoclave was heated to 245° C. by the heater. When the temperature reached 245° C., air was introduced into the autoclave at the gas inlet to replace the nitrogen with the air, and p-tolualdehyde was charged into the autoclave at a rate of 100 g/hr for one hour, while blowing the air into the autoclave.

Even after the completion of charging p-tolualdehyde into the autoclave, the air was continuously blown into the autoclave. When the oxygen concentration of effluent gas was recovered to 21%, the blowing of the air was discontinued, and the reaction product was separated into solid matters and a solution. The solid matters were washed with hot water.

Properties of the resulting terephthalic acid and polymer color shade resulting from the terephthalic acid are given below:
4CBA—221 ppm
$OD_{340}$—0.098
Polymer color shade—Colorless

EXAMPLE 11

Oxidation of p-tolualdehyde was carried out in the same manner as in Example 10, except that 16.7 g of manganese sulfate.$4H_2O$, 7.35 g of sulfuric acid and 31.0 g of sodium bromide were added to an autoclave as the catalysts and 745 g of water was added thereto to make a reaction solution (the amount of reaction solution was 800 g).

Properties of the resulting terephthalic acid and polymer color shade resulting from the terephthalic acid are given below:
4CBA—312 ppm
$OD_{340}$—0.129
Polymer color shade—colorless

COMPARATIVE EXAMPLE 7

Oxidation of p-tolualdehyde was carried out in the same manner as in Example 10, except that 18.4 g of manganese acetate.$4H_2O$, 7.35 g of sulfuric acid, and 31.0 g of sodium bromide were added to an autoclave as the catalysts, and 743 g of water was added thereto to make a reaction solution (the amount of reaction solution was 800 g).

Properties of the resulting terephthalic acid and polymer color shade are given below:
4CBA—2,100 ppm
$OD_{340}$—1.39
Polymer color shade—Brownish yellow In this Example, the amounts of sulfuric acid as the mineral acid, manganese salt and bromine ions were in the preferable ranges of the present invention at the beginning of reaction, but manganese acetate added as the manganese salt was converted to manganese sulfate, etc. during the reaction, and the hydrogen ions originating from the mineral acid was present in the form of acetic acid or lost during the reaction. Thus, the role of mineral acid as referred to herein was no more shown.

COMPARATIVE EXAMPLE 8

Unstable manganese acetate was used as the manganese salt as in Comparative Example 7.

Oxidation of p-tolualdehyde was carried out in the same manner as in Example 10, except that 18.4 g of manganese acetate.$4H_2O$, 12.0 g of hydrogen bromide, and 15.5 g of sodium bromide were added to an autoclave as catalysts, and 754 g of water was added thereto to make a reaction solution (the amount of reaction solution was 800 g).

Properties of the resulting terephthalic acid and polymer color shade are given below:
4CBA—1056 ppm
$OD_{340}$—1.39
Polymer color shade—Brownish Yellow This example is also an example that the manganese salt added is unstable, and thus the hydrogen ions from the mineral acid added failed to show a synergistic action together with the manganese ions, that is, the effect of the present invention.

EXAMPLES 12-14

The same amount of sodium bromide as in Example 11 was used as a bromine ion source, and manganese as cation and hydrogen ions originating from mineral acid were produced from manganese sulfate and sulfuric acid, respectively. Furthermore, a ratio of g-equivalents of hydrogen ions to sum total of g-equivalents of manganese ions and hydrogen ions ($H^+/H^+ + 2Mn^{++}$) was set to 50% while a ratio of sum total of g-equivalents of hydrogen ions and manganese ions to g-equivalents of bromine ions ($H^+ + 2Mn^{++}/Br^-$) was changed. Catalyst composition used, properties of the resulting terephthalic acid and polymer color shade resulting from the terephthalic acid are given in the following Table.

The reaction conditions were same as in Example 11.

| Example | Water (g) | Sodium bromide (g) | Sulfuric acid (g) | Manganese sulfate .$4H_2O$ (g) | Ratio of $2Mn^{++} + H^+/Br^-$ | Terephthalic acid quality | | Polymer color shade |
| --- | --- | --- | --- | --- | --- | --- | --- | --- |
| | | | | | | 4CBA (ppm) | $OD_{340}$ | |
| 12 | 754 | 31.0 | 5.51 | 12.5 | 0.75 | 339 | 0.150 | Colorless |
| 13 | 724 | 31.0 | 14.7 | 33.4 | 2.0 | 234 | 0.061 | Colorless |
| 14 | 676 | 31.0 | 29.4 | 66.8 | 1.0 | 200 | 0.095 | Colorless |

COMPARATIVE EXAMPLE 9

Oxidation of p-tolualdehyde was carried out under the same reaction conditions as in Example 11, except that 31.0 g of sodium bromide, 2.94 g of sulfuric acid, and 6.67 g of manganese sulfate.$4H_2O$ were used as catalysts, and 759 g of water was added thereto as a solvent. The amount of reaction solution was 800 g.

Properties of the resulting terephthalic acid and polymer color shade resulting from the terephthalic acid are given below:
4CBA—483 ppm
$OD_{340}$—0.690
Polymer color shade—Brownish yellow The comparative example shows that the manganese ions and hydrogen ions originating from the mineral acid are short with respect to the bromine ions.

EXAMPLE 15

Oxidation of p-tolualdehyde was carried out under the same conditions as in Example 10, except that 12.0 g of hydrogen bromide and 21.5 g of manganese bromide.$4H_2O$ were used as catalysts, and 766 g of water was added thereto as a solvent (the amount of reaction solution was 800 g), and the reaction temperature was 230° C.

Properties of the resulting terephthalic acid and polymer color shade resulting from the terephthalic acid are given below:

4CBA—374 ppm
$OD_{340}$—0.091
Polymer color shade—colorless

What is claimed is:

1. A process for producing terephthalic acid with a high purity, where terephthalic acid is produced by oxidizing p-tolualdehyde with molecular oxygen in the presence of a heavy metal catalyst and a bromine compound in water as a solvent, characterized by conducting the oxidation at 180°-280° C., using manganese and/or cerium as the heavy metal catalyst, maintaining the bromine concentration in the reaction system during the reaction in a range of 0.5-12% by weight on the basis of the reaction solution in terms of bromine ions, and maintaining the amount of mineral acid in the reaction system during the reaction at a ratio of g-equivalents of hydrogen ions of the mineral acid to sum total of g-equivalents of the hydrogen ions and manganese and/or cerium ions ($H^+/H^+ + 2Mn^{++}$ or $H^+/H^+ + 3Ce^{+++}$) of 1-85%, and at a ratio of sum total of g-equivalents of the hydrogen ions and manganese and/or cerium ions to g-equivalents of bromine ions ($H^+ + 2Mn^{++}/Br^-$ or $H^+ + 3Ce^{+++}/Br^-$) of 0.5-5.

2. A process according to claim 1, characterized in that the bromine compound is manganese bromide, cerium bromide or hydrogen bromide.

3. A process according to claim 1, characterized in that the bromine concentration is maintained in the reaction system during the reaction in a range of 0.5-6% by weight on the basis of the reaction solution in terms of bromine ions.

4. A process according to claim 3, characterized in that the bromine concentration is maintained in the reaction system during the reaction in a range of 1-4% by weight on the basis of the reaction solution in terms of bromine ions.

5. A process according to claim 1, characterized in that the mineral acid is maintained in the reaction system at a ratio of g-equivalents of the hydrogen ions to sum total of g-equivalents of the hydrogen ions and manganese and/or cerium ions ($H^+/H^+ + 2Mn^{++}$ or $H^+/H^+ + 3Ce^{+++}$) of 5-75% and at a ratio of sum total of g-equivalents of the hydrogen ions and manganese and/or cerium ions to g-equivalents of the bromine ions ($H^+ + 2Mn^{++}/Br^-$ or $H^+ + 3Ce^{+++}/Br^-$) of 0.75-4.

6. A process according to claim 1, characterized in that the mineral acid is hydrogen bromide or sulfuric acid.

7. A process according to claim 1, characterized in that the oxidation is carried out at 210°-260° C.

8. A process according to claim 1, characterized in that the oxidation is carried out under a pressure of 10-50 $kg/cm^2$ gauge.

9. A process according to claim 1, characterized in that the oxidation is carried out with air.

10. A process according to claim 1, characterized in that the water as the solvent is used in an amount of at least twice the weight of p-tolualdehyde.

11. A process according to claim 1, characterized in that the water as the solvent is used in an amount of 3-6 times the weight of p-tolualdehyde.

12. A process according to claim 1, characterized in that the oxidation is carried out batchwise, semicontinuously or continuously.

13. A process for preparing terephthalic acid having a high purity, where terephthalic acid is produced by oxidizing p-tolualdehyde with air in the presence of a heavy metal catalyst and a bromine compound in water as a solvent, characterized by conducting the oxidation under a pressure of 10-50 $kg/cm^2$ gauge and at 180°-280° C. by using manganese and/or cerium as the heavy metal catalyst, maintaining the bromine concentration in the reaction system during the reaction in a range of 0.5-12% by weight on the basis of the reaction solution in terms of bromine ions, and maintaining an amount of mineral acid in the reaction system during the reaction to maintain a ratio of g-equivalents of hydrogen ions of the mineral acid to sum total of g-equivalents of the hydrogen ions and manganese and/or cerium ions ($H^+/H^+ + 2Mn^{++}$ or $H^+/H^+ + 3Ce^{+++}$) of 1-85%, and at a ratio of sum total of g-equivalents of the hydrogen ions and manganese and/or cerium ions of g-equivalents of bromine ions ($H^+ + 2Mn^{++}/Br^-$ or $H^+ + 3Ce^{+++}/Br^-$) of 0.5-5.

14. The process of claim 1 in which the terephthalic acid with a high purity is colorless and can be reacted directly, without a prior purification step, with a glycol to obtain a polyester.

15. The process of claim 13 in which the terephthalic acid having a high purity is colorless and can be reacted directly, without a prior purification step, with a glycol to obtain a polyester.

* * * * *